(12) United States Patent
Lee

(10) Patent No.: US 10,787,636 B2
(45) Date of Patent: Sep. 29, 2020

(54) NON-POWERED CONSTANT-TEMPERATURE CELL TRANSFER DEVICE

(71) Applicant: Hyo Young Lee, Seoul (KR)

(72) Inventor: Hyo Young Lee, Seoul (KR)

( * ) Notice: Subject to any disclaimer, the term of this patent is extended or adjusted under 35 U.S.C. 154(b) by 505 days.

(21) Appl. No.: 15/706,355

(22) Filed: Sep. 15, 2017

(65) Prior Publication Data

US 2019/0085281 A1 Mar. 21, 2019

(51) Int. Cl.
| | |
|---|---|
| *C12M 1/00* | (2006.01) |
| *C12M 1/26* | (2006.01) |
| *C12M 1/34* | (2006.01) |

(52) U.S. Cl.
CPC ............ *C12M 41/12* (2013.01); *C12M 29/04* (2013.01); *C12M 33/00* (2013.01); *C12M 41/34* (2013.01)

(58) Field of Classification Search
CPC ...... C12M 29/04; C12M 33/00; C12M 41/12; C12M 41/34
See application file for complete search history.

(56) References Cited

U.S. PATENT DOCUMENTS

2007/0006870 A1* 1/2007 Danforth ................. F24V 30/00
126/263.02

FOREIGN PATENT DOCUMENTS

KR 2016001513 U * 5/2016 ............ C23M 23/00

* cited by examiner

*Primary Examiner* — William H. Beisner
(74) *Attorney, Agent, or Firm* — Weiss & Moy, P.C.; Jeffrey D. Moy

(57) ABSTRACT

The present invention relates to a non-powered constant-temperature cell transfer device, in which a first container, which accommodates living animal cells and a culture solution, is accommodated in a second container having a heat generating unit that emits heat generated by oxidation and reduction reactions of metal by introducing oxygen in the atmosphere in order to continuously provide an optimum culture temperature to a culture container even without being supplied with electric power, thereby maintaining activity and viability of the cells by maintaining a culture environment optimal for proliferation of the cells accommodated in the first container.

48 Claims, 4 Drawing Sheets

【Fig.1】
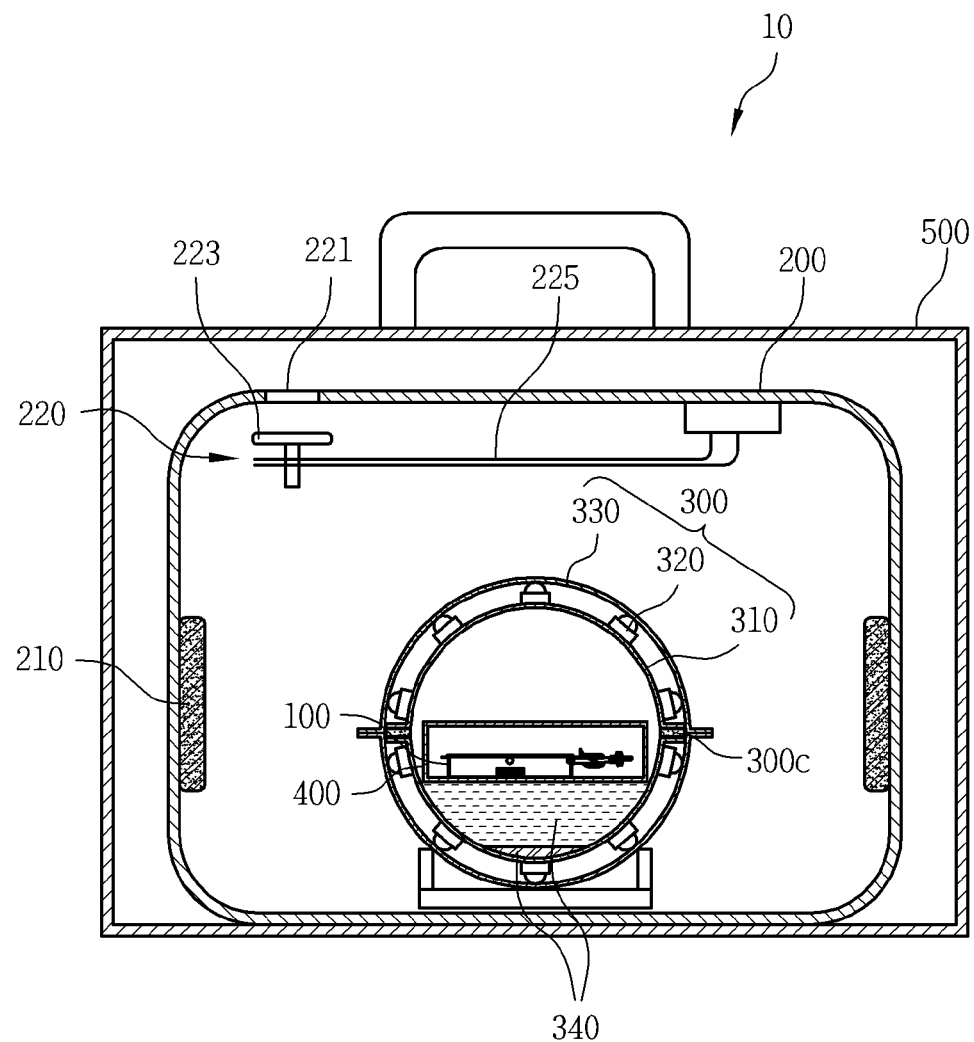

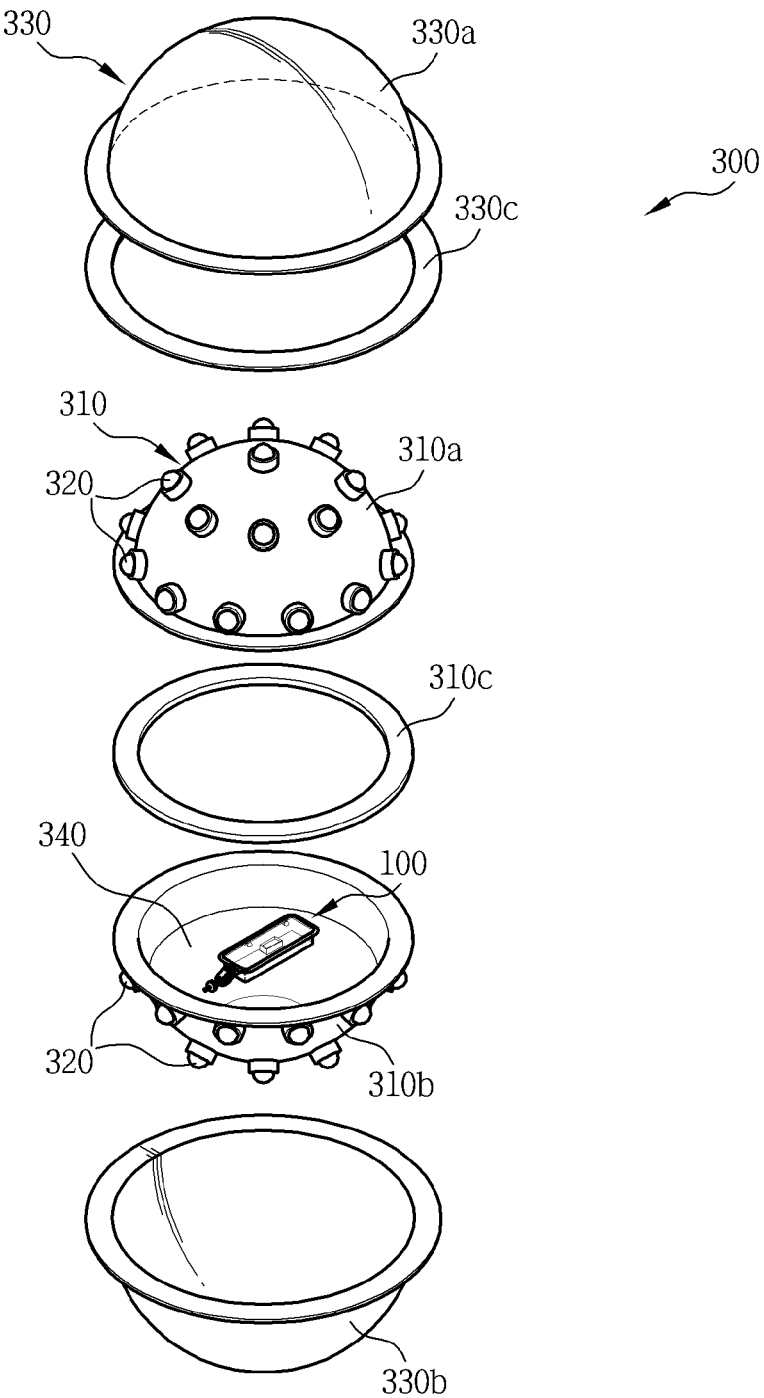
[Fig.2]

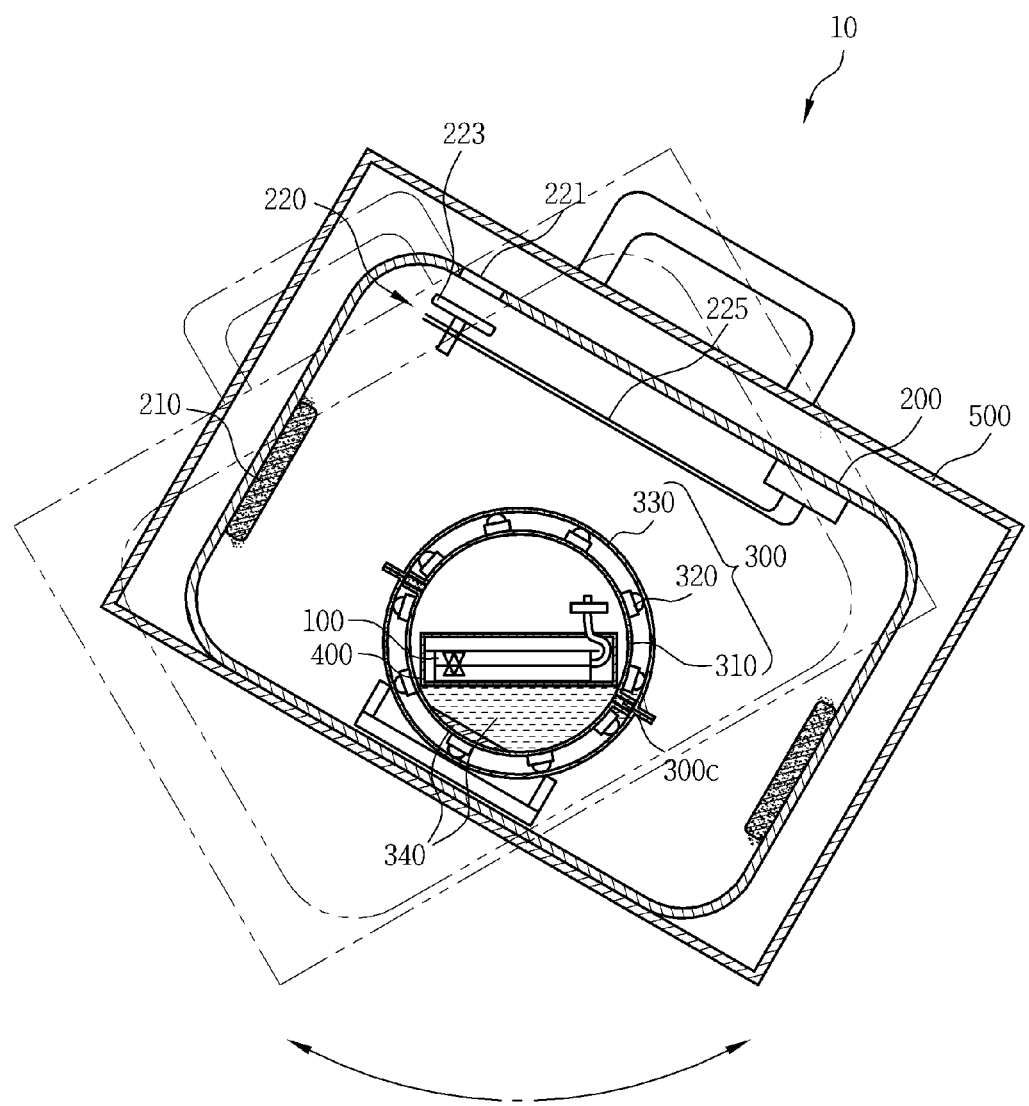
[Fig.3]

[Fig.4]
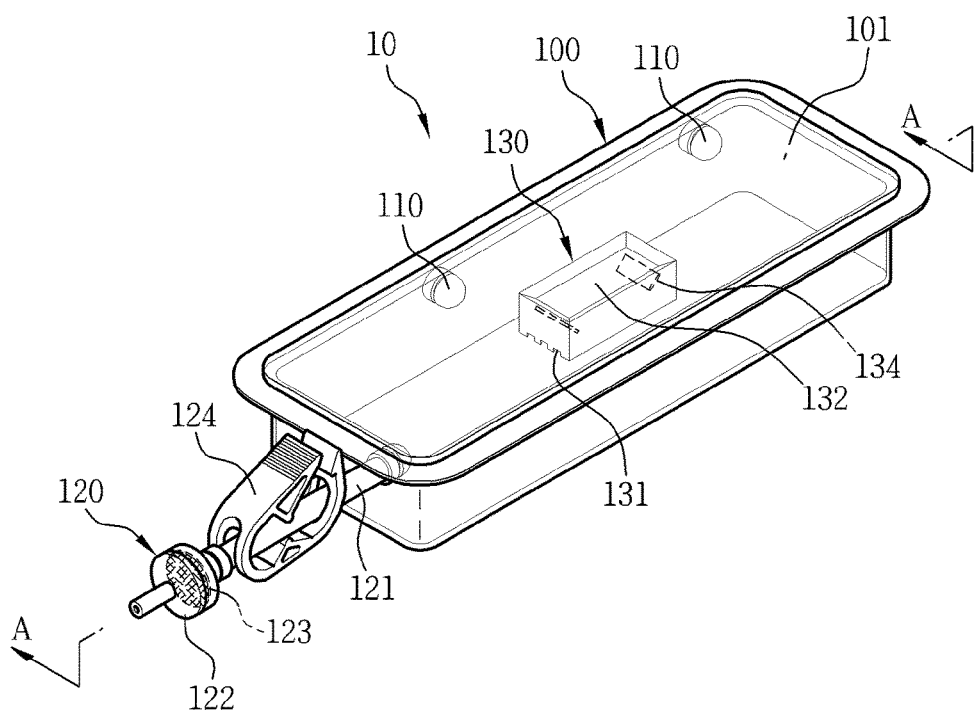
[Fig.5]
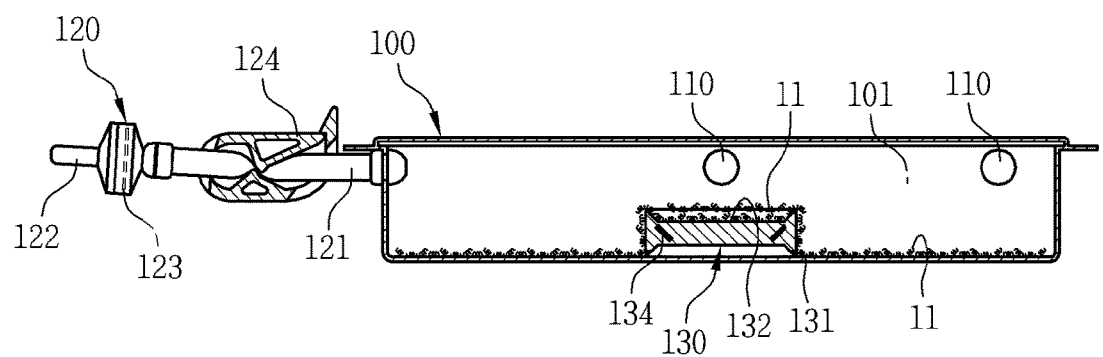

NON-POWERED CONSTANT-TEMPERATURE CELL TRANSFER DEVICE

BACKGROUND OF THE INVENTION

1. Field of the Invention

The present invention relates to a non-powered constant-temperature cell transfer device, and more particularly, to a non-powered constant-temperature cell transfer device capable of transferring cells while providing an optimum culture temperature even without being supplied with electric power, and maintaining a horizontal state of a container for storing the cells even though external impact is applied.

2. Description of the Related Art

In general, cell culture is classified into monolayer culture (attachment culture) in which cells proliferate in a state of being attached to an incubator, and suspension culture in which cells proliferate in a suspended stat.

The cells, which are cultured by using the culture method, react sensitively to a culture environment. The culture environment of the cells is greatly correlated with the cell proliferation and the cell survival. To safely transfer the cells that react sensitively to the culture environment as described above, it is necessary to maintain the culture environment in which the cells may proliferate and survive.

In the case of the general cell culture, it is essential to continuously supply carbon dioxide and maintain a constant temperature and constant humidity. To transfer the cells in the related art, a method of transferring the cells by placing a cell container into liquid nitrogen and maintaining the cells in a low temperature state is used most often.

As disclosed in Korean Patent Application Laid-Open No. 10-2015-0007636, the related art performing the aforementioned functions provides a cell transfer device including a carrier housing which has an accommodation space, a cooling unit which maintains a constant temperature in the carrier housing, a heat dissipation unit which dissipates heat generated during a cooling process of the cooling unit to the outside of the carrier housing, a carrier control unit which controls an operation of the cooling unit and an operation of the heat dissipation unit, and a chargeable power source unit, in which at one side of the carrier housing, there are provided a transfer temperature management device which sets a temperature for a transfer process, displays the temperature, and records a temperature history, a notifying device which enables an operator to recognize an abnormal situation when the abnormal situation occurs during the process of transferring the cells, a GPS receiver which receives a GPS signal in order to ascertain a position of the carrier housing, and a wireless network module which connects a wireless network with the Internet.

However, the technical configurations in the related art have the following problems.

There is a problem in that activity and viability of the cells deteriorate when cooling and transferring the cells.

In addition, there is a problem in that a device for maintaining a temperature for storing the cells needs to be necessarily supplied with electric power.

Furthermore, there is a problem in that a horizontal state of a container for storing the cells cannot be maintained.

RELATED ART DOCUMENT

Patent Document (Patent Document 1) Korean Patent Application Laid-Open No. 10-2015-0007636 (Jan. 21, 2015)

SUMMARY OF THE INVENTION

The present invention has been made in an effort to solve the problems in the related art, and an object of the present invention is to continuously provide an optimum culture temperature to a culture container even without being supplied with electric power.

Another object of the present invention is to maintain an optimum culture temperature even without being supplied with electric power.

Yet another object of the present invention is to transfer cells while maintaining a horizontal state of a container for containing the cells even though external impact is applied.

According to an aspect of the present invention, there is provided a non-powered constant-temperature cell transfer device, wherein a first container accommodating living animal cells and a culture solution is accommodated in a second container having a heat generating unit that emits heat generated by oxidation and reduction reactions of metal by introducing oxygen in the atmosphere, such that the first container is transferred while maintaining a physiologically active temperature of the cells accommodated in the first container.

According to another aspect of the present invention, there is provided a non-powered constant-temperature cell transfer device, wherein a third container, which accommodates a first container accommodating living animal cells and a culture solution so as to maintain a horizontal state of the first container, is installed in a second container having a heat generating unit that emits heat generated by oxidation and reduction reactions of metal by introducing oxygen in the atmosphere, such that the cells are transferred while maintaining a physiologically active temperature of the cells accommodated in the first container by the second container, and an inclination of the first container is minimized by the third container.

According to yet another aspect of the present invention, there is provided a non-powered constant-temperature cell transfer device, wherein a third container, which accommodates a first container accommodating living animal cells and a culture solution so as to maintain a horizontal state of the first container, is installed in a second container having a heat generating unit that emits heat generated by oxidation and reduction reactions of metal by introducing oxygen in the atmosphere, such that the cells are transferred while maintaining a physiologically active temperature of the cells accommodated in the first container by the second container, an inclination of the first container is minimized by the third container, and the third container is charged with carbon dioxide with concentration higher than concentration of carbon dioxide in the atmosphere.

In an embodiment of the present invention, the first container may have a space of which the hermetic state is selectively determined, such that processes of injecting the culture solution into the space, inoculating the cells, separating the cells, and obtaining the cells are enabled in the hermetic state of the space, and a process of culturing the cells is enabled in an opened state of the space.

In an embodiment of the present invention, the first container may include: a hermetic passageway which loads a fluid, gas, and the cells into the space from the outside and unload the fluid, the gas, and the cells to the outside; a circulation filter which circulates the gas required for cell culture in the space; and a scraper which is installed in the space, scrapes the cells while moving, and separates the cells from a bottom surface of the space.

In an embodiment of the present invention, the first container may have carbon dioxide with concentration of 1% to 30%.

In an embodiment of the present invention, the third container may have carbon dioxide with concentration of 1% to 30%.

In an embodiment of the present invention, a temperature in the first container may be maintained to 22° C. to 43° C. by the heat generating unit.

In an embodiment of the present invention, the heat generating unit may generate heat at 40° C. to 60° C. by the oxidation and reduction reactions between metal and oxygen in the atmosphere introduced into the second container.

In an embodiment of the present invention, a thermal insulating material may be mixed with metal powder that generates heat while reacting with oxygen in the heat generating unit.

In an embodiment of the present invention, the second container may further include an opening and closing unit which determines an inflow of oxygen in the atmosphere.

In an embodiment of the present invention, the third container may include: an inner container which has a spherical shape and has a weight member installed on a bottom of the inner container so that the first container is seated on the weight member; an outer container which has a spherical shape and accommodates the inner container; and a plurality of wheels which is installed to roll between the inner container and the outer container.

In an embodiment of the present invention, the non-powered constant-temperature cell transfer device may further include a fourth container which hermetically accommodates the first container.

In an embodiment of the present invention, the thermal insulating material may be made by selectively mixing one or more materials selected from a group consisting of sawdust, salt, and moisture.

In an embodiment of the present invention, the opening and closing unit may include: an inlet hole which penetrates one side of the second container and allows oxygen in the atmosphere to be introduced into the second container; a closure which selectively opens and closes the inlet hole; and an opening and closing member which is installed on the closure and blocks an inflow of oxygen when a temperature in the second container is increased.

In an embodiment of the present invention, the outer container and the inner container may define a spherical shape as a hemispheric first auxiliary container and a hemispheric second auxiliary container are assembled, and a packing may be provided between the first auxiliary container and the second auxiliary container.

In an embodiment of the present invention, the weight member may be made of a fluid.

In an embodiment of the present invention, the weight member may include: a solid which has a self-weight; and a fluid which is accommodated at an upper side of the solid.

In an embodiment of the present invention, a bimetal material or a temperature reactive linear material may be applied to the opening and closing member.

In an embodiment of the present invention, a cylinder or a piston may be applied to the opening and closing member.

As described above, according to the non-powered constant-temperature cell transfer device according to the exemplary embodiment of the present invention, the first container, which accommodates the living animal cells and the culture solution, is accommodated in the second container having the heat generating unit that emits heat generated by the oxidation and reduction reactions of metal by introducing oxygen in the atmosphere in order to continuously provide an optimum culture temperature to the culture container even without being supplied with electric power, thereby maintaining activity and viability of the cells by maintaining a culture environment optimal for proliferation of the cells accommodated in the first container.

In addition, according to the non-powered constant-temperature cell transfer device of the present invention, the second container further includes the opening and closing unit which determines an inflow of oxygen in the atmosphere in order to maintain an optimum culture temperature even without being supplied with electric power, such that the opening and closing unit automatically blocks the inflow of oxygen to decrease the temperature in the container when the temperature in the container is increased, and the opening and closing unit allows the inflow of oxygen when the temperature in the container is decreased to a preset temperature, thereby maintaining an optimum temperature for cell culture.

Furthermore, according to the non-powered constant-temperature cell transfer device of the present invention, the third container, which includes the inner container having the weight member installed therein, the outer container for accommodating the inner container, and the plurality of wheels installed to roll between the inner container and the outer container, is installed in the second container in order to transfer the cells while maintaining the horizontal state of the container for storing the cells even though external impact is applied, and as a result, the horizontal state of the first container, which accommodates the living animal cells and the culture solution, is maintained even though a bag sways or tilts when transferring the cells.

BRIEF DESCRIPTION OF THE DRAWINGS

FIG. 1 is a cross-sectional view illustrating a non-powered constant-temperature cell transfer device of the present invention.

FIG. 2 is an exploded perspective view illustrating a third container of the non-powered constant-temperature cell transfer device of the present invention.

FIG. 3 is a perspective view illustrating a first container of the non-powered constant-temperature cell transfer device of the present invention.

FIG. 4 is a cross-sectional view illustrating the first container of the non-powered constant-temperature cell transfer device of the present invention.

FIG. 5 is a cross-sectional view illustrating a state in which the non-powered constant-temperature cell transfer device of the present invention is used.

DETAILED DESCRIPTION OF THE PREFERRED EMBODIMENT

Hereinafter, the present invention will be described in detail with reference to the accompanying drawings. First, it should be noted that in the drawings, like constituent elements or components are referred by like reference numerals if possible. In the description of the present invention, the specific descriptions of publicly known related function or configurations will be omitted in order to prevent the specific descriptions from obscuring the subject matter of the present invention.

FIG. 1 is a cross-sectional view illustrating a non-powered constant-temperature cell transfer device of the present invention, FIG. 2 is an exploded perspective view illustrating a third container of the non-powered constant-temperature cell transfer device of the present invention, FIG. 3 is a perspective view illustrating a first container of the non-powered constant-temperature cell transfer device of the present invention, FIG. 4 is a cross-sectional view illustrating the first container of the non-powered constant-temperature cell transfer device of the present invention, and FIG. 5 is a cross-sectional view illustrating a state in which the non-powered constant-temperature cell transfer device of the present invention is used.

First, as illustrated in FIG. 1, in a configured state of a non-powered constant-temperature cell transfer device 10 according to the present invention, a first container 100, which accommodates living animal cells 11 and a culture solution 12, is accommodated in a second container 200 having a heat generating unit 210 that emits heat generated by oxidation and reduction reactions of metal by introducing oxygen from the atmosphere, such that the first container 100 may be transferred while maintaining a physiologically active temperature of the cells 11 accommodated in the first container 100.

In addition, in another aspect of the present invention, there is provided the non-powered constant-temperature cell transfer device 10 in which a third container 300, which accommodates the first container 100 and maintains a horizontal state of the first container 100 that accommodates the living animal cells 11 and the culture solution 12, is installed in the second container 200 having the heat generating unit 210 that emits heat generated by the oxidation and reduction reactions of metal by introducing oxygen from the atmosphere, such that the cells 11 may be transferred with the second container 200 while maintaining the physiologically active temperature of the cells 11 accommodated in the first container 100, and an inclination of the first container 100 is minimized by the third container 300.

Furthermore, in yet another aspect of the present invention, there is provided the non-powered constant-temperature cell transfer device 10 in which a third container 300, which accommodates the first container 100 and maintains a horizontal state of the first container 100 that accommodates the living animal cells 11 and the culture solution 12, is installed in the second container 200 having the heat generating unit 210 that emits heat generated by the oxidation and reduction reactions of metal by introducing oxygen from the atmosphere, such that the cells 11 may be transferred with the second container 200 while maintaining the physiologically active temperature of the cells 11 accommodated in the first container 100, an inclination of the first container 100 is minimized by the third container 300, and the third container 300 is charged with carbon dioxide with concentration higher than concentration of carbon oxide in the atmosphere.

The non-powered constant-temperature cell transfer device 10 according to the present invention will be described below in more detail.

Referring to FIG. 1, the non-powered constant-temperature cell transfer device 10 according to the exemplary embodiment of the present invention includes the first container 100 and the second container 200.

In this case, as illustrated in FIGS. 3 and 4, the first container 100 accommodates the living animal cells 11 and the culture solution 12.

The culture container 100 has therein a hermetic space 101.

The culture container 100 is made of a soft plastic material, such that a size of the space 101 may be changed by external pressure or force.

As the culture container 100, the culture container 100, which has the space of which the hermetic state may be selectively determined, is provided, such that processes of injecting the culture solution into the space 101, inoculating the cells, separating the cells, and obtaining the cells are enabled in the hermetic state of the space 101, and a process of culturing the cells is enabled in an opened state of the space.

In addition, during the process of obtaining the cells 11, the cells 11 are obtained except for some of the entire cultured cells 11, such that the cells 11 remaining in the culture container 100 may be repeatedly cultured.

Furthermore, after obtaining the entire cultured cells during the process of obtaining the cells 11, the processes of injecting the culture solution into the culture container 100, inoculating the cells, culturing the cells, separating the cells, and obtaining the cells may be repeatedly performed.

Hermetic passageways 110 and a circulation filter 120 are mounted on the culture container 100 in order to enable the continuous culture of the cells 11.

First, the hermetic passageways 110 are installed on the culture container 100 to enable the processes of injecting the culture solution 12 into the space 101, inoculating the culture solution 12 with the cells 11, and obtaining the cells 11, and even during these processes, the hermetic state of the hermetic container is maintained.

That is, the hermetic passageways 110 are installed on lateral surfaces of the culture container 100 so that a fluid, gas, and the cell 11 may be loaded into the space 101 from the outside and unloaded to the outside of the space 101.

To this end, the hermetic passageways 110 are installed on the surface of the culture container 100, and the hermetic passageways 110 are formed in the form of a block made of a soft material and installed in the space 101.

In this case, the process of injecting the culture solution 12 and the cells 11 through the hermetic passageways 110 and the process of obtaining the cells 11 to the outside are typically performed by using a syringe.

In other words, a needle of the syringe is penetratively inserted into the hermetic passageway 110, and then the culture solution 12 accommodated in the syringe is injected into the space 101, or the cells 11, which are cultured in the culture container 100 and separated, are drawn into the syringe by using negative pressure of the syringe so that the cells 11 may be obtained to the outside.

Further, when the needle is withdrawn from the hermetic passageway 110 after injecting the culture solution 12 or obtaining the cells 11, the hermetic passageway 110 is sealed by itself because of elasticity of the hermetic passageway 110, thereby maintaining sealability of the space 101.

In addition, the circulation filter 120 is installed to inject gas, which is required to culture the cells 11, into the space 101 of the culture container 100.

That is, the culture container 100 is stored in the culture environment means 200 during the process of culturing the cells 11, such that an appropriate temperature is provided to the culture container 100, and the gas required to culture the cells 11 is provided to the culture container 100.

In this case, the culture container 100 allows the gas to be introduced into the space 101 or discharged to the outside of the space 101 through the circulation filter 120.

That is, regarding the entrance of the gas into the space 101 of the culture container 100, the gas required to culture the cells 11 may be introduced into the space 101, that is, into the culture environment means 200 through the circulation filter 120 by generating negative pressure in the culture environment means 200 so that the size of the space 101 of the culture container 100 is changed.

Here, the gas includes any one or more of carbon dioxide and oxygen.

A specific configuration of the circulation filter 120 will be described below.

The circulation filter 120 includes a tube 121 which is installed at a side of the culture container 100, a valve 122 which is installed at an end of the tube 121, and a filter 123 which is installed in the valve 122.

Further, a clip 124 may be mounted on the tube 121 to selectively close and open the tube 121.

The clip 124 opens the tube 121 to enable the gas to be introduced into the space 101 when accommodating the culture container 100 in the culture environment means 200, and the tube 121 is closed by using the clip 124 to close the space 101 of the hermetic container in order to unload the culture container 100 from the culture environment means 200.

Further, because the cultured cells 11 on a bottom surface of the space 101 of the culture container 100 are not easily separated due to attachment force, a scraper 130, which is a separate tool for separating the cells 11, is installed in the space 101.

That is, the scraper 130 scrapes the cells 11 to separate the cells 11 from the bottom surface of the space 101 while rotating or moving in the space 101 by mechanical external force, magnetic force, potential energy, or the like.

In this case, a method of separating the cells 11 by using the magnetic force will be described below.

A movable member 140, which is provided separately, is placed close to a lower surface of an outer portion of the culture container 100 and connected to the scraper 130 through magnetic force, and the scraper 130 is moved in the space 101 in conjunction with the movement of the movable member 140, such that the scraper 130 causes friction to scrape and separate the cells 11.

That is, each of the scraper 130 and the movable member 140 has a metallic body 134 or a magnetic body 141, such that the movements of the scraper 130 and the movable member 140 may be integrally performed in conjunction with each other by magnetic force.

Further, in the method of separating the cells 11 by using the potential energy, the culture container 100 is positioned to be inclined so that the scraper 130 having a self-weight scrapes and separates the cells 11 while sliding on the bottom surface of the space 101.

A culture groove 132 is formed at an upper side of the scraper 130 configured as described above, such that the culture groove 132 may be charged with the culture solution 12 and the cells 11 may be cultured in the culture groove 132.

In particular, the scraper 130 has a quadrangular culture container, but the shape of the culture container is not limited, and may be a circular shape or a polygonal shape such as a triangular shape as long as the scraper 130 has a surface to which the cells may be attached.

Further, the scraper 130 has a lower surface which is in contact with the bottom surface of the space 101 and forms a plurality of blades 131.

Here, the lower surface of the scraper 130, which is in contact with the bottom surface of the space 101, forms the plurality of blades 131, and the blades 131 are formed to have edge angles so as to separate the cells 11 from the bottom surface by friction with the bottom surface of the space 101.

Alternatively, the lower surface of the scraper 130, which is in contact with the bottom surface of the space 101, forms the plurality of blades 131, the blades 131 are formed so that edge angles are continuously formed, such that the blades 131 are in contact or non-contact with the bottom surface of the space 101.

In addition, the scraper is made of a material selected from polyethylene (PE), polypropylene (PP), polyamide (PA), polyacetal (POM), polyvinyl chloride (PVC), polyester (PET), polymethylpentene (PMP), ionomer (IO), ethylene vinyl alcohol (EVOH), polyvinyl chloride (PVA), polystyrene (PS), methacrylic resin (PMMA), polycarbonate (PC), polyvinyl acetate (PVAc), polyvinyl alcohol (PVA), phenol resin (PF), urea resin (UF), melamine resin (MF), epoxy resin (EP), polyurethane (PUR), unsaturated polyester resin (UP), and metal.

Meanwhile, the first container 100 is accommodated in the second container 200. The heat generating unit 210, which emits heat generated by the oxidation and reduction reactions of metal by introducing oxygen in the atmosphere, is provided in the second container 200. That is, the first container 100 may be transferred while maintaining a physiologically active temperature of the cells 11 accommodated in the first container 100.

Furthermore, the heat generating unit 210 generates heat at 40° C. to 60° C. through the oxidation and reduction reactions between the metal and oxygen introduced into the second container 200 from the atmosphere. In this case, in the heat generating unit 210, a thermal insulating material is mixed with metal powder that generates heat while reacting with oxygen. Here, the thermal insulating material is made by selectively mixing one or more materials selected from a group consisting of sawdust, salt, and moisture.

That is, a temperature in the first container 100 is maintained to 22° C. to 43° C. by the heat generating unit 210.

As a result, in the non-powered constant-temperature cell transfer device 10 according to the exemplary embodiment of the present invention, the first container 100, which accommodates the living animal cells 11 and the culture solution 12, is accommodated in the second container 200 having the heat generating unit 210 that emits heat generated by the oxidation and reduction reactions of metal by introducing oxygen in the atmosphere in order to continuously provide an optimum culture temperature to the culture container even without being supplied with electric power, thereby maintaining activity and viability of the cells by maintaining a culture environment optimal for proliferation of the cells 11 accommodated in the first container 100.

Furthermore, an opening and closing unit 220, which determines an inflow of oxygen in the atmosphere, is further included in the second container 200. The opening and closing unit 220 includes an inlet hole 221 which penetrates one side of the second container 200 and allows oxygen in the atmosphere to be introduced into the second container 200, a closure 223 which selectively opens and closes the inlet hole 221, and an opening and closing member 225 which is installed on the closure 223 and blocks an inflow of oxygen when the temperature in the second container 200 is increased.

Furthermore, a bimetal material or a temperature reactive linear member is applied to the opening and closing member 225. In addition, a cylinder or a piston is applied to the opening and closing member 225.

As a result, in the non-powered constant-temperature cell transfer device 10 of the present invention, the second container 200 further includes the opening and closing unit 220 which determines an inflow of oxygen in the atmosphere in order to maintain an optimum culture temperature even without being supplied with electric power, such that the opening and closing unit 220 automatically blocks the inflow of oxygen to decrease the temperature in the container when the temperature in the container is increased, and the opening and closing unit 220 allows the inflow of oxygen when the temperature in the container is decreased to a preset temperature, thereby maintaining an optimum temperature for cell culture.

Meanwhile, the third container 300, which accommodates the first container 100 accommodating the living animal cells 11 and the culture solution 12 in order to maintain a horizontal state of the first container 100, is installed in the second container 200.

As illustrated in FIG. 2, the third container 300 includes an inner container 310 which has a spherical shape and has a weight member 340 installed on a bottom of the inner container 310 so that the first container 100 is seated on the weight member 340, an outer container 330 which has a spherical shape and accommodates the inner container 310, and a plurality of wheels 320 which is installed to roll between the inner container 310 and the outer container 330.

Further, the outer container 330 and the inner container 310 define the spherical shape as a hemispheric first auxiliary container 300a and a hemispheric second auxiliary container 300b are assembled, and a packing 300c is provided between the first auxiliary container 300a and the second auxiliary container 300b.

Furthermore, the weight member 340 is made of a fluid or a solid. In particular, the weight member 340 includes a solid having a self-weight, and a fluid accommodated at an upper side of the solid.

As a result, as illustrated in FIG. 5, in the non-powered constant-temperature cell transfer device 10 of the present invention, the third container 300, which includes the inner container 310 having the weight member 340 installed therein, the outer container 330 for accommodating the inner container 310, and the plurality of wheels 320 installed to roll between the inner container 310 and the outer container 330, is installed in the second container 200 in order to transfer the cells while maintaining the horizontal state of the container for storing the cells even though external impact is applied, and as a result, the horizontal state of the first container 100, which accommodates the living animal cells 11 and the culture solution 12, is maintained even though a bag sways or tilts when transferring the cells.

Meanwhile, a fourth container 400 for hermetically accommodating the first container 100 is further included. The fourth container 400 may be a hermetic container.

In particular, the first container 100 and the third container 300 have carbon dioxide with concentration of 1% to 30%.

Words of degree, such as "about", "substantially", and the like are used in the present specification in the sense of "at, or nearly at, when given the manufacturing, design, and material tolerances inherent in the stated circumstances" and are used to prevent the unscrupulous infringer from unfairly taking advantage of the invention disclosure where exact or absolute figures and operational or structural relationships are stated as an aid to understanding the invention.

The present invention, which has been described above, is not limited by the aforementioned exemplary embodiment and the accompanying drawings, and it is obvious to those skilled in the art to which the present invention pertains that various substitutions, modifications and alterations may be made without departing from the technical spirit of the present invention.

What is claimed is:

1. A non-powered constant-temperature cell transfer device, wherein a first container accommodating living animal cells and a culture solution is accommodated in a second container having a heat generating unit that emits heat generated by oxidation and reduction reactions of metal by introducing oxygen in the atmosphere, such that the first container is transferred while maintaining a physiologically active temperature of the cells accommodated in the first container; wherein the second container has an opening and closing unit which determines an inflow of oxygen in the atmosphere.

2. The non-powered constant-temperature cell transfer device of claim 1, wherein the first container has a space of which the hermetic state is selectively determined, such that processes of injecting the culture solution into the space, inoculating the cells, separating the cells, and obtaining the cells are enabled in the hermetic state of the space, and a process of culturing the cells is enabled in an opened state of the space.

3. The non-powered constant-temperature cell transfer device of claim 1, wherein the first container comprises:
a hermetic passageway which loads a fluid, gas, and the cells into the space from the outside and unload the fluid, the gas, and the cells to the outside;
a circulation filter which circulates the gas required for cell culture in the space; and
a scraper which is installed in the space, scrapes the cells while moving, and separates the cells from a bottom surface of the space.

4. The non-powered constant-temperature cell transfer device of claim 1, wherein the first container has carbon dioxide with concentration of 1% to 30%.

5. The non-powered constant-temperature cell transfer device of claim 1, wherein a third container has carbon dioxide with concentration of 1% to 30%.

6. The non-powered constant-temperature cell transfer device of claim 1, wherein a temperature in the first container is maintained to 22° C. to 43° C. by the heat generating unit.

7. The non-powered constant-temperature cell transfer device of claim 1, wherein the heat generating unit generates heat at 40° C. to 60° C. by the oxidation and reduction reactions between metal and oxygen in the atmosphere introduced into the second container.

8. The non-powered constant-temperature cell transfer device of claim 1, wherein a thermal insulating material is mixed with metal powder that generates heat while reacting with oxygen in the heat generating unit.

9. The non-powered constant-temperature cell transfer device of claim 8, wherein the thermal insulating material is made by selectively mixing one or more materials selected from a group consisting of sawdust, salt, and moisture.

10. The non-powered constant-temperature cell transfer device of claim 9, wherein the opening and closing unit comprises:

an inlet hole which penetrates one side of the second container and allows oxygen in the atmosphere to be introduced into the second container;

a closure which selectively opens and closes the inlet hole; and an opening and closing member which is installed on the closure and blocks an inflow of oxygen when a temperature in the second container is increased.

11. The non-powered constant-temperature cell transfer device of claim 10, wherein a bimetal material or a temperature reactive linear material is applied to the opening and closing member.

12. The non-powered constant-temperature cell transfer device of claim 10, wherein a cylinder or a piston is applied to the opening and closing member.

13. A non-powered constant-temperature cell transfer device, wherein a third container, which accommodates a first container accommodating living animal cells and a culture solution so as to maintain a horizontal state of the first container, is installed in a second container having a heat generating unit that emits heat generated by oxidation and reduction reactions of metal by introducing oxygen in the atmosphere, such that the cells are transferred while maintaining a physiologically active temperature of the cells accommodated in the first container by the second container, and an inclination of the first container is minimized by the third container.

14. The non-powered constant-temperature cell transfer device of claim 13, wherein the first container has a space of which the hermetic state is selectively determined, such that processes of injecting the culture solution into the space, inoculating the cells, separating the cells, and obtaining the cells are enabled in the hermetic state of the space, and a process of culturing the cells is enabled in an opened state of the space.

15. The non-powered constant-temperature cell transfer device of claim 13, wherein the first container comprises:
a hermetic passageway which loads a fluid, gas, and the cells into the space from the outside and unload the fluid, the gas, and the cells to the outside;
a circulation filter which circulates the gas required for cell culture in the space; and
a scraper which is installed in the space, scrapes the cells while moving, and separates the cells from a bottom surface of the space.

16. The non-powered constant-temperature cell transfer device of claim 13, wherein the first container has carbon dioxide with concentration of 1% to 30%.

17. The non-powered constant-temperature cell transfer device of claim 13, wherein the third container has carbon dioxide with concentration of 1 to 30%.

18. The non-powered constant-temperature cell transfer device of claim 13, wherein a temperature in the first container is maintained to 22° C. to 43° C. by the heat generating unit.

19. The non-powered constant-temperature cell transfer device of claim 13, wherein the heat generating unit generates heat at 40° C. to 60° C. by the oxidation and reduction reactions between metal and oxygen in the atmosphere introduced into the second container.

20. The non-powered constant-temperature cell transfer device of claim 13, wherein a thermal insulating material is mixed with metal powder that generates heat while reacting with oxygen in the heat generating unit.

21. The non-powered constant-temperature cell transfer device of claim 20, wherein the thermal insulating material is made by selectively mixing one or more materials selected from a group consisting of sawdust, salt, and moisture.

22. The non-powered constant-temperature cell transfer device of claim 13, wherein the second container further comprises an opening and closing unit which determines an inflow of oxygen in the atmosphere.

23. The non-powered constant-temperature cell transfer device of claim 22, wherein the opening and closing unit comprises:
an inlet hole which penetrates one side of the second container and allows oxygen in the atmosphere to be introduced into the second container;
a closure which selectively opens and closes the inlet hole; and
an opening and closing member which is installed on the closure and blocks an inflow of oxygen when a temperature in the second container is increased.

24. The non-powered constant-temperature cell transfer device of claim 23, wherein a bimetal material or a temperature reactive linear material is applied to the opening and closing member.

25. The non-powered constant-temperature cell transfer device of claim 23, wherein a cylinder or a piston is applied to the opening and closing member.

26. The non-powered constant-temperature cell transfer device of claim 13, wherein the third container comprises:
an inner container which has a spherical shape and has a weight member installed on a bottom of the inner container so that the first container is seated on the weight member;
an outer container which has a spherical shape and accommodates the inner container; and
a plurality of wheels which is installed to roll between the inner container and the outer container.

27. The non-powered constant-temperature cell transfer device of claim 26, wherein the outer container and the inner container define a spherical shape as a hemispheric first auxiliary container and a hemispheric second auxiliary container are assembled, and a packing is provided between the first auxiliary container and the second auxiliary container.

28. The non-powered constant-temperature cell transfer device of claim 26, wherein the weight member is made of a fluid.

29. The non-powered constant-temperature cell transfer device of claim 26, wherein the weight member comprises:
a solid which has a self-weight; and
a fluid which is accommodated at an upper side of the solid.

30. The non-powered constant-temperature cell transfer device of claim 13, further comprises:
a fourth container which hermetically accommodates the first container.

31. A non-powered constant-temperature cell transfer device, wherein a third container, which accommodates a first container accommodating living animal cells and a culture solution so as to maintain a horizontal state of the first container, is installed in a second container having a heat generating unit that emits heat generated by oxidation and reduction reactions of metal by introducing oxygen in the atmosphere, such that the cells are transferred while maintaining a physiologically active temperature of the cells accommodated in the first container by the second container, an inclination of the first container is minimized by the third container, and the third container is charged with carbon dioxide with concentration higher than concentration of carbon dioxide in the atmosphere.

32. The non-powered constant-temperature cell transfer device of claim 31, wherein the first container has a space of which the hermetic state is selectively determined, such that processes of injecting the culture solution into the space, inoculating the cells, separating the cells, and obtaining the cells are enabled in the hermetic state of the space, and a process of culturing the cells is enabled in an opened state of the space.

33. The non-powered constant-temperature cell transfer device of claim 31, wherein the first container comprises:
  a hermetic passageway which loads a fluid, gas, and the cells into the space from the outside and unload the fluid, the gas, and the cells to the outside;
  a circulation filter which circulates the gas required for cell culture in the space; and
  a scraper which is installed in the space, scrapes the cells while moving, and separates the cells from a bottom surface of the space.

34. The non-powered constant-temperature cell transfer device of claim 31, wherein the first container has carbon dioxide with concentration of 1% to 30%.

35. The non-powered constant-temperature cell transfer device of claim 31, wherein the third container has carbon dioxide with concentration of 1% to 30%.

36. The non-powered constant-temperature cell transfer device of claim 31, wherein a temperature in the first container is maintained to 22° C. to 43° C. by the heat generating unit.

37. The non-powered constant-temperature cell transfer device of claim 31, wherein the heat generating unit generates heat at 40° C. to 60° C. by the oxidation and reduction reactions between metal and oxygen in the atmosphere introduced into the second container.

38. The non-powered constant-temperature cell transfer device of claim 31, wherein a thermal insulating material is mixed with metal powder that generates heat while reacting with oxygen in the heat generating unit.

39. The non-powered constant-temperature cell transfer device of claim 38, wherein the thermal insulating material is made by selectively mixing one or more materials selected from a group consisting of sawdust, salt, and moisture.

40. The non-powered constant-temperature cell transfer device of claim 31, wherein the second container further comprises an opening and closing unit which determines an inflow of oxygen in the atmosphere.

41. The non-powered constant-temperature cell transfer device of claim 40, wherein the opening and closing unit comprises:
  an inlet hole which penetrates one side of the second container and allows oxygen in the atmosphere to be introduced into the second container;
  a closure which selectively opens and closes the inlet hole; and
  an opening and closing member which is installed on the closure and blocks an inflow of oxygen when a temperature in the second container is increased.

42. The non-powered constant-temperature cell transfer device of claim 41, wherein a bimetal material or a temperature reactive linear material is applied to the opening and closing member.

43. The non-powered constant-temperature cell transfer device of claim 41, wherein a cylinder or a piston is applied to the opening and closing member.

44. The non-powered constant-temperature cell transfer device of claim 31, wherein the third container comprises:
  an inner container which has a spherical shape and has a weight member installed on a bottom of the inner container so that the first container is seated on the weight member;
  an outer container which has a spherical shape and accommodates the inner container; and
  a plurality of wheels which is installed to roll between the inner container and the outer container.

45. The non-powered constant-temperature cell transfer device of claim 44, wherein the outer container and the inner container define a spherical shape as a hemispheric first auxiliary container and a hemispheric second auxiliary container are assembled, and a packing is provided between the first auxiliary container and the second auxiliary container.

46. The non-powered constant-temperature cell transfer device of claim 44, wherein the weight member is made of a fluid.

47. The non-powered constant-temperature cell transfer device of claim 44, wherein the weight member comprises:
  a solid which has a self-weight; and
  a fluid which is accommodated at an upper side of the solid.

48. The non-powered constant-temperature cell transfer device of claim 31, further comprises:
  a fourth container which hermetically accommodates the first container.

* * * * *